United States Patent
Munns et al.

(10) Patent No.: US 8,373,075 B2
(45) Date of Patent: Feb. 12, 2013

(54) IMPLANTABLE CO-FIRED ELECTRICAL FEEDTHROUGHS

(75) Inventors: Gordon Orvis Munns, Stacy, MN (US); Greg Haubrich, Champlin, MN (US); David B. Engmark, Bethel, MN (US); Joyce Yamamoto, Maple Grove, MN (US); Simon Goldman, St. Louis Park, MN (US); William Michael Brosnan, Rogers, MN (US); Brad Conrad Tischendorf, Minneapolis, MN (US); Andrew Jason Thom, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 321 days.

(21) Appl. No.: 12/608,443

(22) Filed: Oct. 29, 2009

(65) Prior Publication Data
US 2011/0102967 A1    May 5, 2011

(51) Int. Cl.
*H05K 1/16* (2006.01)
*H05K 1/03* (2006.01)
*H01R 9/00* (2006.01)
(52) U.S. Cl. ......... 174/260; 174/255; 361/765; 361/772
(58) Field of Classification Search .................. None
See application file for complete search history.

(56) References Cited

U.S. PATENT DOCUMENTS

| | | | |
|---|---|---|---|
| 5,132,648 A | 7/1992 | Trinh et al. | |
| 5,620,476 A | 4/1997 | Truex et al. | |
| 5,683,435 A | 11/1997 | Truex et al. | |
| 5,782,891 A | 7/1998 | Hassler et al. | |
| 6,020,562 A * | 2/2000 | Burns et al. | 174/261 |
| 6,052,623 A | 4/2000 | Fenner et al. | |
| 6,414,835 B1 | 7/2002 | Wolf et al. | |
| 7,068,491 B1 | 6/2006 | Burdon et al. | |
| 7,186,926 B2 * | 3/2007 | Maeno | 174/260 |
| 7,746,661 B2 * | 6/2010 | Liao et al. | 361/777 |
| 2007/0060969 A1 | 3/2007 | Burdon et al. | |
| 2007/0123949 A1 | 5/2007 | Dabney et al. | |
| 2007/0179553 A1 | 8/2007 | Iyer et al. | |
| 2007/0179554 A1 | 8/2007 | Iyer et al. | |
| 2007/0203530 A1 | 8/2007 | Hubing et al. | |
| 2007/0239223 A1 | 10/2007 | Engmark et al. | |
| 2008/0119906 A1 | 5/2008 | Starke | |
| 2010/0168818 A1 | 7/2010 | Barror et al. | |

OTHER PUBLICATIONS (PCT/US2010/053905) PCT Notification of Transmittal of the International Search Report and the Written Opinion of the International Searching Authority.

* cited by examiner

*Primary Examiner* — Jayprakash N Gandhi
*Assistant Examiner* — Dion Ferguson

(57) ABSTRACT

A multilayered feedthrough for an implantable medical device includes a substrate having a first edge, a second edge, and a substrate length. A plurality of traces is formed on the substrate and extends along the substrate length. The plurality of traces extends to the first and second edges of the substrate. An insulator layer is formed on the substrate and the plurality of traces. A ground plane layer is formed on the insulator layer.

29 Claims, 7 Drawing Sheets

IMPLANTABLE CO-FIRED ELECTRICAL FEEDTHROUGHS

FIELD

The present disclosure relates to electrical interconnects for implantable medical systems and devices, and, more particularly, to a co-fired ceramic electrical feedthrough assembly.

INTRODUCTION

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Miniaturized electrical feedthroughs are required for implantable medical devices (IMDs) that offer reduced functional volume in a small package while offering a high level of electromagnetic interference (EMI) protection. In conventional feedthrough technologies, EMI filtering is oftentimes accomplished by mounting chip-type capacitors or discoidal capacitors on the surface of an electrical feedthrough. This technology suffers from the disadvantage of increasing overall device volume while increasing lead interconnect length required to attach the termination of the capacitor to the hermetic pin assembly and grounding structure (typically the ferrule and a portion of the outer enclosure of a metallic IMD). Technologies are required that enable integration of EMI protection while improving the electrical performance in a very small, low-profile, miniaturized device structure.

The present teachings provide a feedthrough assembly of the type used, for example, in implantable medical devices such as heart pacemakers and the like, wherein the feedthrough assembly is constructed of a plurality of layers of a non-conductive material with conductive traces present thereon.

SUMMARY

In various exemplary embodiments, the present disclosure relates to a multilayered feedthrough for an implantable medical device. The multilayered feedthrough includes a first edge and a second edge, and further includes a substrate having a first edge, a second edge, and a substrate length. A plurality of traces is formed on the substrate and extends along the substrate length. A plurality of contact pads is electrically coupled with the plurality of traces and extends to the first and second edges of the substrate. An insulator layer is formed on the substrate and the plurality of traces. The feedthrough further includes a ground plane layer.

In various exemplary embodiments, the present disclosure relates to a multilayered feedthrough for an implantable medical device. The multilayered feedthrough includes a substrate having a first edge, a second edge, a substrate length, a first surface and a second surface opposite the first surface. A first plurality of traces is formed on the first surface and extends along the substrate length. A second plurality of traces is formed on the second surface and extends along the substrate length. A first plurality of contact pads is electrically coupled with the first plurality of traces and extends to the first and second edges of the substrate. A second plurality of contact pads is electrically coupled with the second plurality of traces and extends to the first and second edges of the substrate. A first insulator layer is formed on the first surface and the first plurality of traces. A second insulator layer is formed on the second surface and the second plurality of traces. The feedthrough further includes first and second ground plane layers.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF DRAWINGS

The present disclosure will become more fully understood from the detailed description and the accompanying drawings, wherein.

DESCRIPTION

Figure 1:
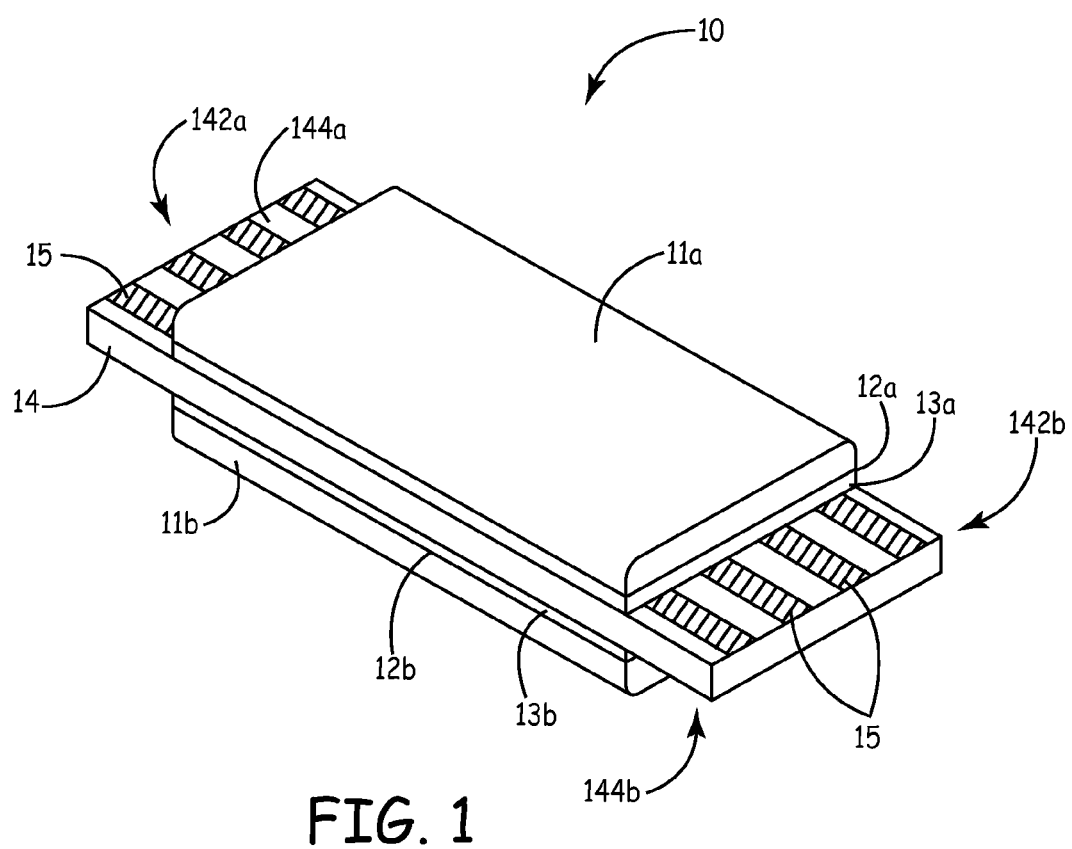
FIGS. 1 and 2 are isometric and exploded views, respectively, of a feedthrough assembly according to various embodiments of the present disclosure.

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method can be executed in different order without altering the principles of the present disclosure.

Figure 2:
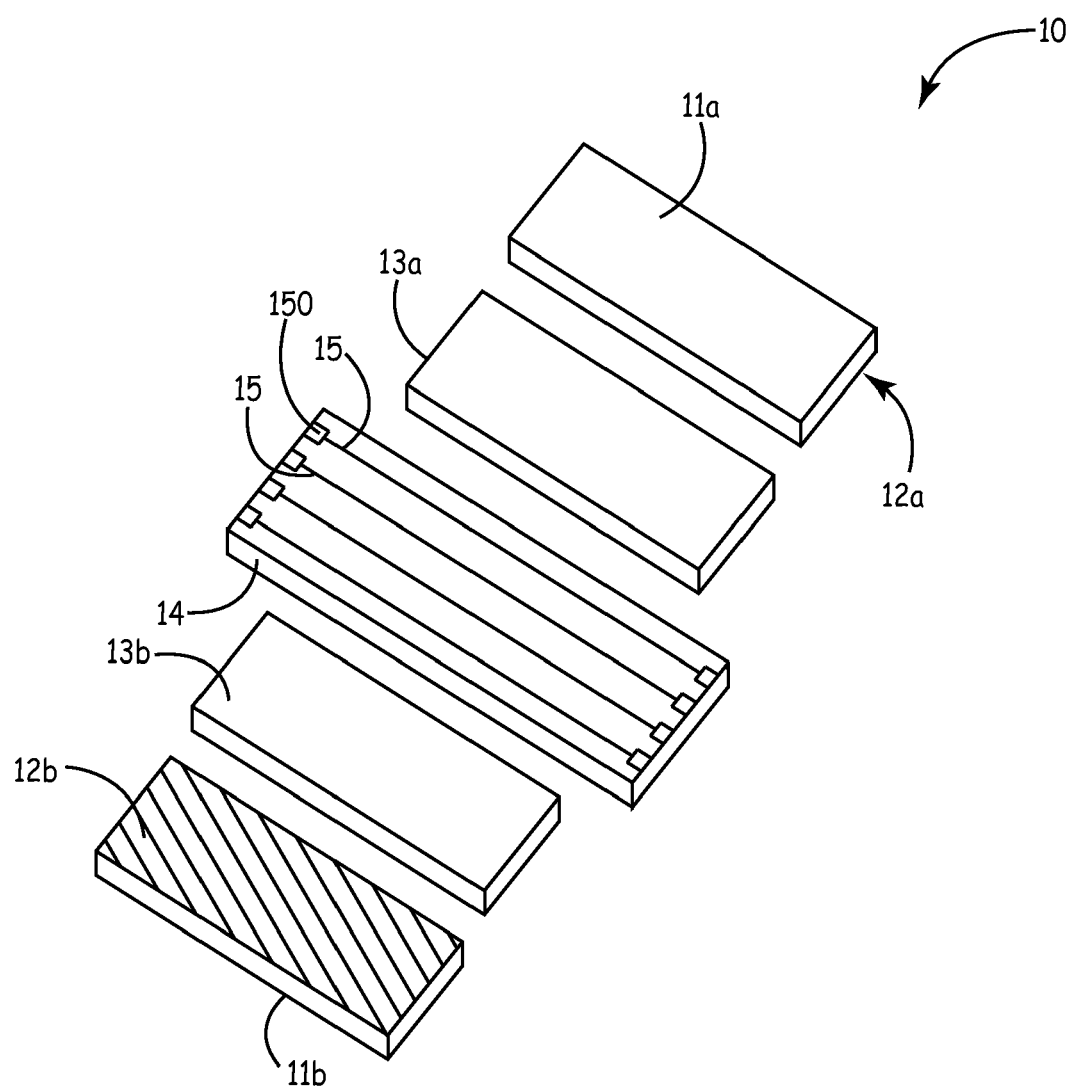

Referring now to FIGS. 1 and 2, a feedthrough assembly 10 according to various embodiments of the present disclosure as illustrated. The feedthrough assembly 10 includes a plurality of layers. A substrate 14 includes a plurality of traces 15 formed on one or both sides of the substrate 14. The substrate 14 can be made of any non-conductive material, for example, a high temperature co-fired ceramic or other ceramic material. The traces 15 can be formed on the substrate 14 by depositing a conductive material, such as platinum, gold or palladium, on the surface of substrate 14 such that they extend from one edge of the substrate to the other. Other methods of forming traces 15 can be utilized.

The traces 15 can be formed on a first surface 144*a* and/or a second surface 144*b* of the substrate 14. In various embodiments, integrated devices such as capacitors and/or filtering devices, e.g., SAW filters, can be formed (for example, by screening or photo lithography processes) on the substrate 14 or applied to the substrate 14, and electrically connected to the traces 15/contact pads 150. For example, a SAW filter can be made from various materials, such as lithium niobate or lithium tantalate, and surface mounted to the substrate 14. In this case, the insulator layer(s), which are described below, can encase the SAW filter to serve as a hermetic housing.

An insulator layer 13a, 13b can be formed on the first and second surfaces 144a, 144b, respectively. The insulator layer can be formed of any non-conductive material, such as a high temperature co-fired ceramic or other ceramic material, similar to the substrate 14. In some embodiments, the insulator layers 13a, 13b can be formed of any biostable and biocompatible materials, e.g., alumina, zirconia or a combination thereof. In various embodiments, the insulator layer 13a, 13b covers only a portion of the first and second surfaces 144a, 144b of the substrate 14. For example, substrate edges 142a, 142b can remain exposed and not covered by insulator layer 13a, 13b. In this manner, traces 15 can be electrically connected to the IMD.

Ground planes 12a, 12b can be formed on the insulator layer 13a, 13b in various embodiments. The ground planes 12a, 12b can be formed of any conductive material, such as platinum, gold, palladium or other metal. The ground planes 12a, 12b assist in shielding the traces 15 from stray electromagnetic interference, as well as minimizing interference between the traces 15 themselves. In various embodiments, the ground planes 12a, 12b can be formed of a continuous layer of conductive material covering the insulator layers 13a, 13b. In some embodiments, the ground planes 12a, 12b can be formed of a mesh or grid of conductive material covering the insulator layers 13a, 13b. Another insulator layer 11a, 11b can be formed on the ground planes 12a, 12b to insulate the ground planes 12a, 12b from the IMD.

While the illustrated embodiments show the ground planes 12a, 12b to be formed on layers separate from substrate 14, the present disclosure encompasses the formation of ground planes 12a, 12b in different configurations. For example, ground planes 12a, 12b can be formed on the substrate 14 and electrically insulated from traces 15. Furthermore, ground planes 12a, 12b can be formed to substantially surround the substrate 14 and/or be oriented perpendicular to the first and second surfaces 144a, 144b of substrate 14. Ground planes 12a, 12b can be connected to electrical ground potential in various ways, for example, by connection with one or more of the traces 15, one or more of the contact pads 150, with a weld ring 35 (described more fully below) or a combination thereof. For example only, ground planes 12a, 12b can be connected with traces 15 through the use of one or more vias formed in an insulator layers or layers 11a, 11b. The use of vias is described more fully below with respect to FIGS. 6-7.

Figure 3:
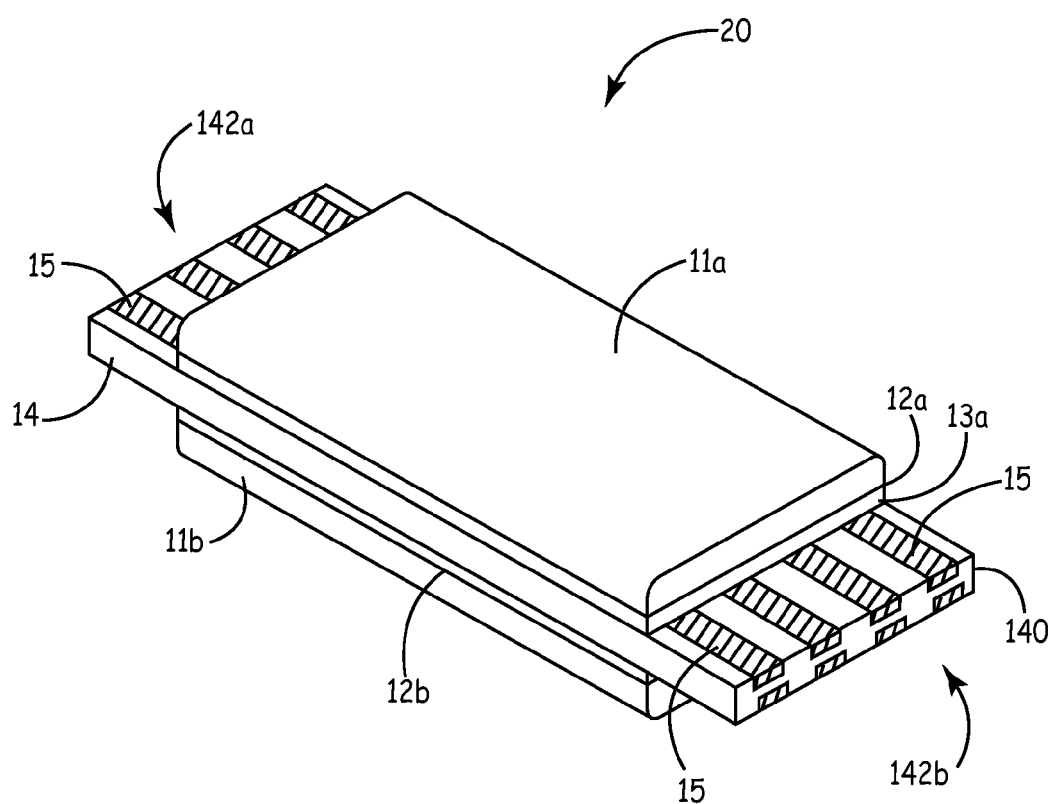
FIG. 3 is an isometric view of a feedthrough assembly according to various embodiments of the present disclosure.

The traces 15 of the feedthrough assembly 10 can extend to the edges 142a, 142b of the substrate 14. In this manner, the traces 15 can be utilized as card edge connectors to mate with corresponding receiver slots (not shown) present, e.g., in the IMD. In various embodiments, contact pads 150 are included as part of the traces 15. The contact pads 150 can have a larger surface area than traces 15 such that positive coupling between the traces and the associated circuitry of the IMD can be assured. In various embodiments, the traces 15/contact pads 150 can extend around the edges 142a, 142b and be present on end surfaces 140 of the substrate 14, as shown in FIG. 3. The presence of the traces 15, with or without contact pads 150, on the end surfaces 140 can provide a more consistent coupling between the feedthrough assembly 10 and the receiver slots of the IMD.

Figure 4:
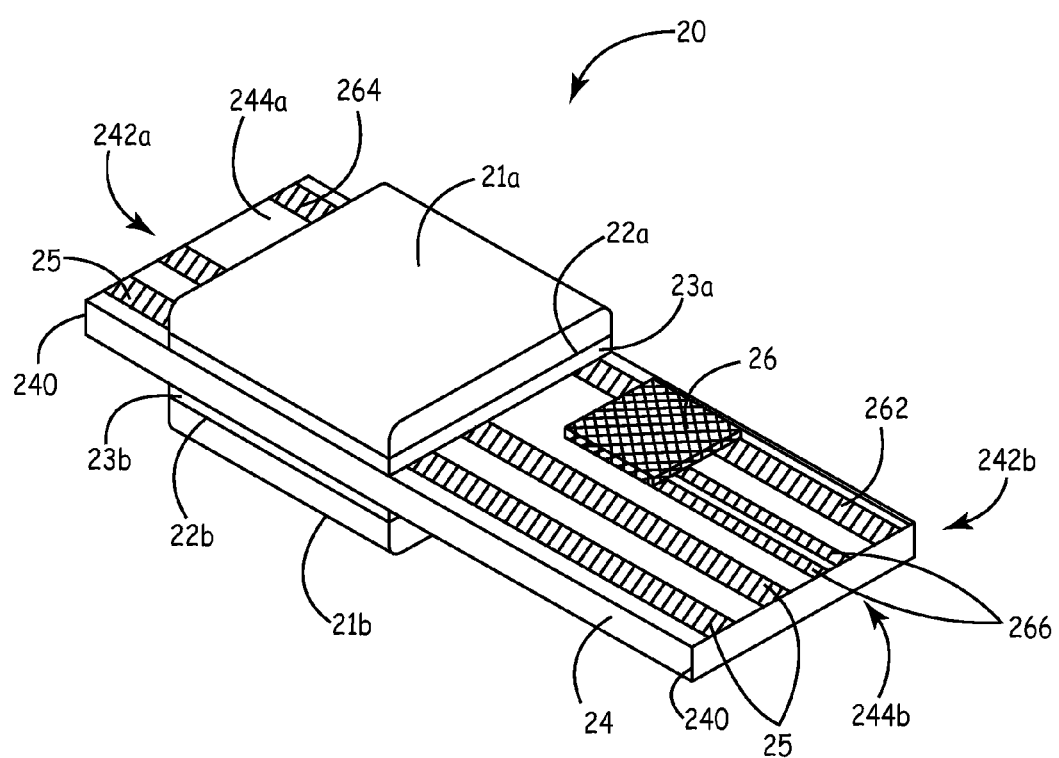
FIG. 4 is an isometric view of a feedthrough assembly with an integrated transceiver according to various embodiments of the present disclosure.

Referring now to FIG. 4, a feedthrough assembly 20 with an integrated transceiver 26 according to various embodiments of the present disclosure as illustrated. Similar to feedthrough assembly 10 discussed above, the feedthrough assembly 20 includes a plurality of layers. A substrate 24 includes a plurality of traces 25 formed on one or both sides of the substrate 24. The substrate 24 can be made of any non-conductive material, for example, a high temperature co-fired ceramic or other ceramic material. The traces 25 can be formed on the substrate 24 by depositing a conductive material, such as platinum, gold or palladium, on the surface of substrate 24 such that they extend from one edge of the substrate to the other. Other methods of forming traces 25 can be utilized. The traces 25 can be formed on a first surface 244a and/or a second surface 244b of the substrate 14. The traces 25 can include contact pads, similar to that described above in regard to traces 15 and contact pads 150. In various embodiments, integrated devices such as capacitors and/or filtering devices, e.g., SAW filters, can be formed on the substrate 24 and electrically connected to the traces 25.

An insulator layer 23a, 23b can be formed on the first and second surfaces 244a, 244b, respectively. The insulator layer can be formed of any non-conductive material, such as, a high temperature co-fired ceramic or other ceramic material, similar to the substrate 24. In various embodiments, the insulator layer 23a, 23b covers only a portion of the first and second surfaces 244a, 244b of the substrate 24. Substrate edges 242a, 242b can remain exposed and not covered by insulator layer 23a, 23b. In this manner, traces 25 can be electrically connected to the IMD.

Ground planes 22a, 22b can be formed on the insulator layer 23a, 23b in various embodiments. The ground planes 22a, 22b can be formed of any conductive material, such as platinum, gold, palladium or other metal. The ground planes 22a, 22b assist in shielding the traces 25 from stray electromagnetic interference, as well as minimizing interference between the traces 25 themselves. In various embodiments, the ground planes 22a, 22b can be formed of a continuous layer of conductive material covering the insulator layers 23a, 23b. In some embodiments, another insulator layer 21a, 21b is formed on the ground planes 22a, 22b to insulate the ground planes 22a, 22b from the IMD. As described above, ground planes 22a, 22b can be connected to electrical ground potential in various ways, for example, by connection with one or more of the traces 25, one or more of the contact pads 150, with a weld ring 35 (described more fully below) or a combination thereof.

The traces 25 of the feedthrough assembly 20 can extend to the edges 242a, 242b of the substrate 24. In this manner, the traces 25 can be utilized as card edge connectors to mate with corresponding receiver slots (not shown) present, e.g., in the IMD. In various embodiments, the traces 25 can extend to around the edges 242a, 242b and be present on end surfaces 240 of the substrate 24, as shown in FIG. 3 with respect to feedthrough assembly 10. The presence of the traces 25 on the end surfaces 240 can provide a more consistent coupling between the feedthrough assembly 20 and the receiver slots of the IMD.

An integrated transceiver 26 can be surface mounted on the substrate 24, as illustrated in FIG. 4. A signal-in trace 262 can be electrically connected to integrated transceiver 26 from the IMD. In this manner, integrated transceiver 26 can receive signals from the IMD. Integrated transceiver 26 can be further electrically connected to a signal-out trace 264. Signal-out trace 264 can be electrically connected to an antenna or transmission/reception element (not shown). In this manner, integrated transceiver 26 can transmit information received from the IMD to, as well as receive information from, a remote device. Integrated transceiver 26 can be powered by power lines 266 formed as traces on substrate 24. In various embodiments, transceiver 26 can include power lines and/or include signal-in and signal-out lines that are separate from the substrate 24 and traces 25 formed thereon, such as with a wire or ribbon bond.

Figure 5:
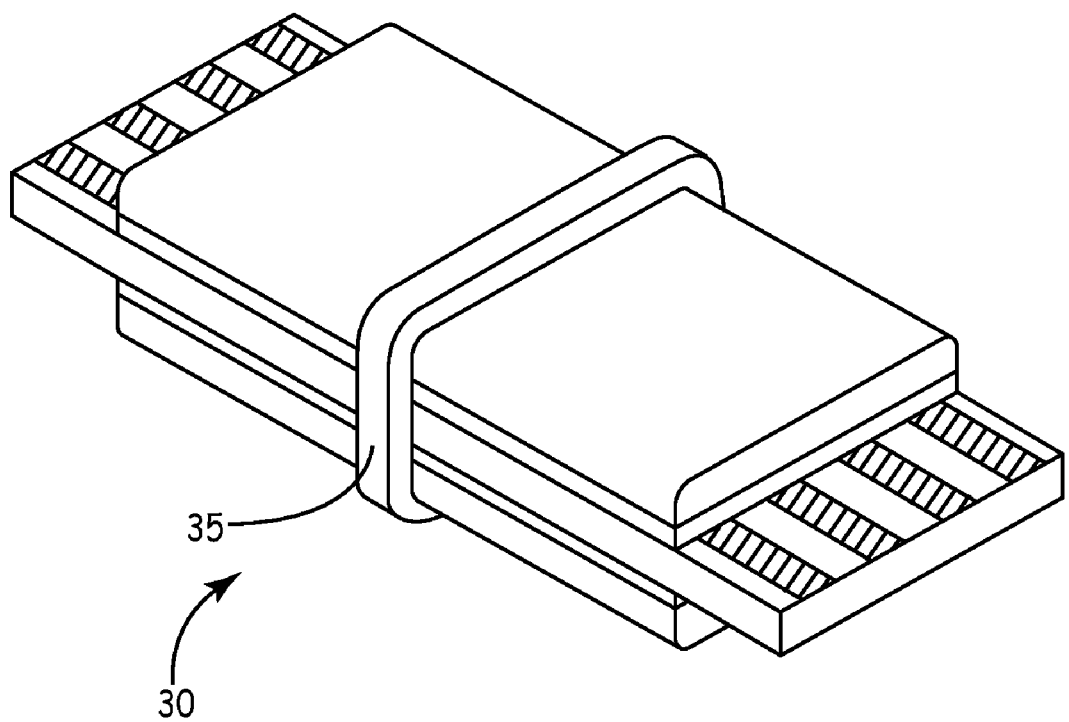
FIG. 5 is an isometric view of a feedthrough assembly with attached weld ring according to various embodiments of the present disclosure.

Referring now to FIG. 5, a feedthrough assembly 30 according to various embodiments of the present disclosure as illustrated. Feedthrough assembly 30 can be substantially similar to feedthrough assemblies 10 and 20 described above. Weld ring 35 can be hermetically sealed to feedthrough assembly 30. Weld ring 35 can be can be made of any biostable and biocompatible material, for example, titanium, niobium, tantalum or combinations thereof. Weld ring 35 can also be connected to the body of IMD such that there is a hermetic seal between IMD and feedthrough assembly 30. The weld ring 35 can be coupled to the feedthrough assembly in various manners, such as by braze joint, diffusion bond, glass seal or a compression seal.

Figure 6:
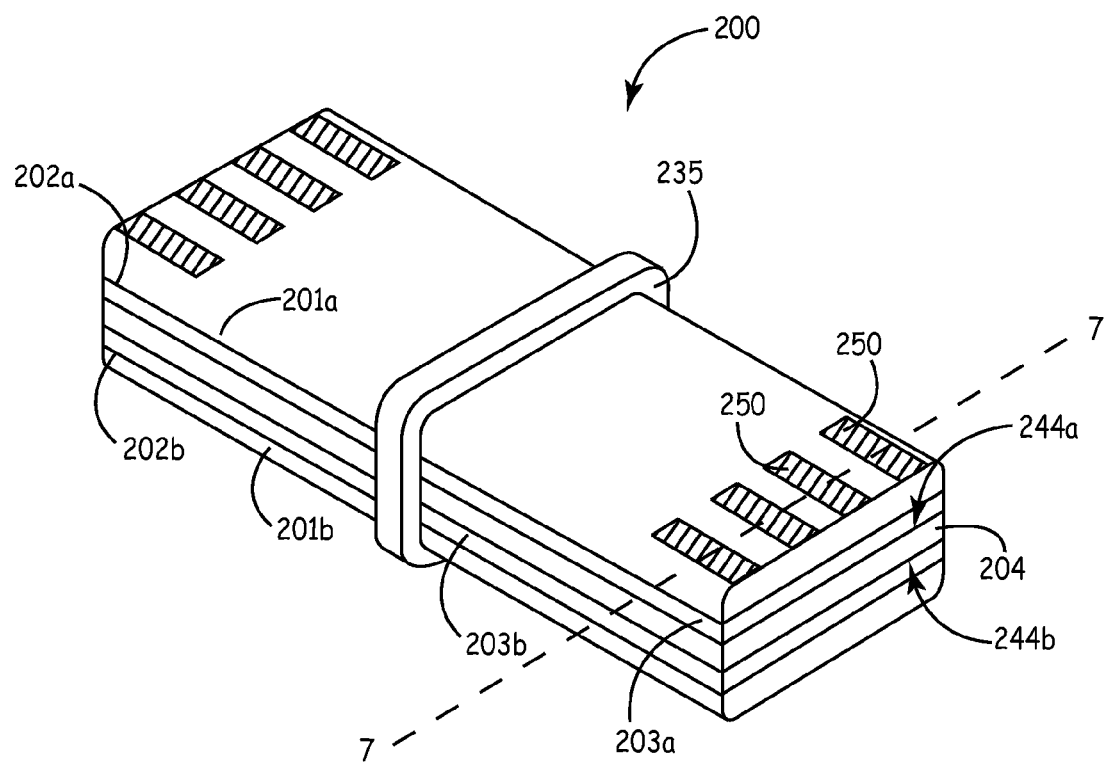
FIG. 6 is an isometric view of a feedthrough assembly according to various embodiments of the present disclosure.
Figure 7:
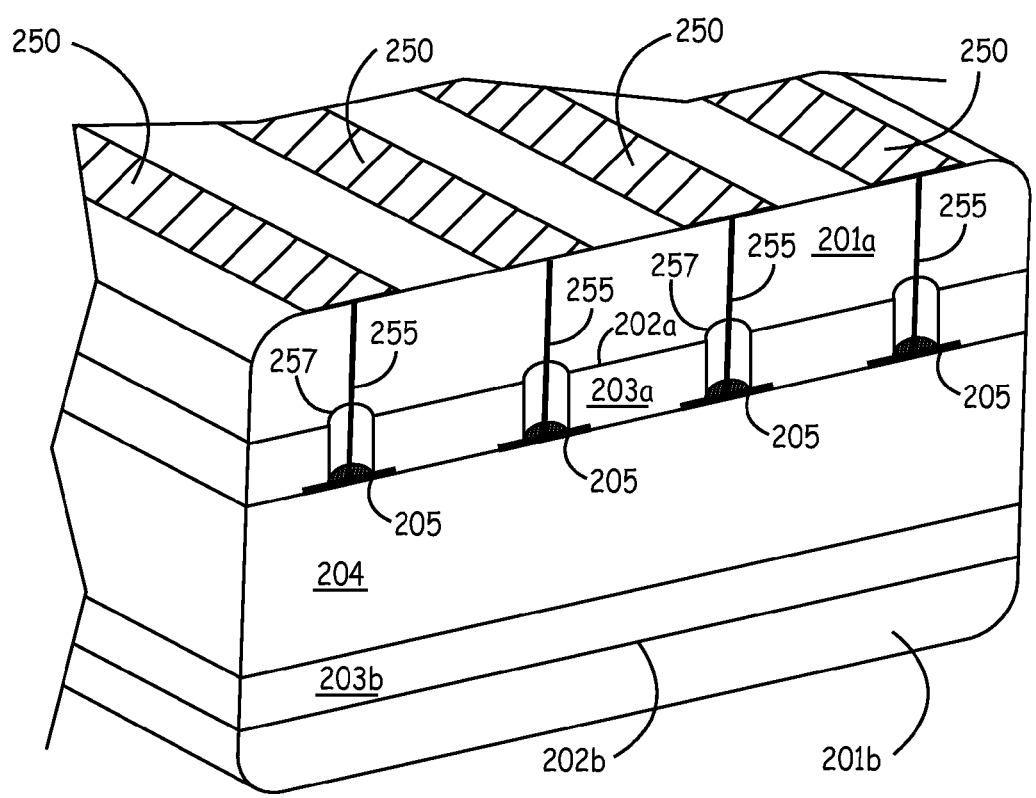
FIG. 7 is a cross-sectional view of the feedthrough assembly of FIG. 6 along line 7-7.

Referring now to FIGS. 6 and 7, a feedthrough assembly 200 according to various embodiments of the present disclosure as illustrated. The feedthrough assembly 200 includes a plurality of layers. A substrate 204 includes a plurality of traces 205 (FIG. 7) formed on one or both sides of the substrate 204. The substrate 204 can be made of any non-conductive material, for example, a high temperature co-fired ceramic or other ceramic material. The traces 205 can be formed on the substrate 204 by depositing a conductive material, such as platinum, gold or palladium, on the surface of substrate 204. Other methods of forming traces 205 can be utilized.

The traces 205 can be formed on a first surface 244a and/or a second surface 244b of the substrate 204. In various embodiments, integrated devices such as capacitors and/or filtering devices, e.g., SAW filters, can be formed (for example, by screening or photo lithography processes) on the substrate 204 or applied to the substrate 204, and electrically connected to the traces 205/contact pads 250. For example, a SAW filter can be made from various materials, such as lithium niobate or lithium tantalate, and surface mounted to the substrate 204. In this case, the insulator layer(s), which are described below, can encase the SAW filter to serve as a hermetic housing.

An insulator layer 203a, 203b can be formed on the first and second surfaces 244a, 244b, respectively. The insulator layer can be formed of any non-conductive material, such as a high temperature co-fired ceramic or other ceramic material, similar to the substrate 204. In some embodiments, the insulator layers 203a, 203b can be formed of any biostable and biocompatible materials, e.g., alumina, zirconia or a combination thereof. In various embodiments, the insulator layer 203a, 203b covers the entire first and second surfaces 244a, 244b of the substrate 204.

Ground planes 202a, 202b can be formed on the insulator layer 203a, 203b in various embodiments. The ground planes 202a, 202b can be formed of any conductive material, such as platinum, gold, palladium or other metal. The ground planes 202a, 202b assist in shielding the traces 205 from stray electromagnetic interference, as well as minimizing interference between the traces 205 themselves. In various embodiments, the ground planes 202a, 202b can be formed of a continuous layer of conductive material covering the insulator layers 203a, 203b. In some embodiments, the ground planes 202a, 202b can be formed of a mesh or grid of conductive material covering the insulator layers 203a, 203b. Another insulator layer 201a, 201b can be formed on the ground planes 202a, 202b to insulate the ground planes 202a, 202b from the IMD. While the illustrated embodiments show the ground planes 202a, 202b to be formed on layers separate from substrate 204, the present disclosure encompasses the formation of ground planes 202a, 202b in different configurations. For example, ground planes 202a, 202b can be formed on the substrate 204 and electrically insulated from traces 205. Furthermore, ground planes 202a, 202b can be formed to substantially surround the substrate 204 and/or be oriented perpendicular to the first and second surfaces 244a, 244b of substrate 204. As described above, ground planes 202a, 202b can be connected to electrical ground potential in various ways, for example, by connection with one or more traces 205, one or more contact pads 250, a weld ring 35 (described more fully below) or a combination thereof.

In various embodiments, the traces 205 of the feedthrough assembly 200 do not extend to the edges of the substrate 204. Instead, contact pads 250 are formed on a separate layer (in the illustrated example, insulator layer 201a) and electrically coupled with traces 205. In this manner, the contact pads 250 can be utilized as card edge connectors to mate with corresponding receiver slots (not shown) present, e.g., in the IMD. The contact pads 250 can have a larger surface area than traces 205 such that positive coupling between the traces and the associated circuitry of the IMD can be assured. In various embodiments, the contact pads 250 can extend around the edges of the feedthrough assembly, similar to feedthrough assembly 20 illustrated in FIG. 3. The presence of the contact pads 250 on the end surfaces can provide a more consistent coupling between the feedthrough assembly 200 and the receiver slots of the IMD.

The traces 205 can be electrically coupled with the contact pads 250 by vias 255. Vias 255 extend between the various layers of feedthrough assembly 200, and can be formed of any conductive material, such as platinum, gold, palladium or other metal. In the illustrated embodiment, vias 255 extend through insulator layer 201a, ground plane 202a and insulator layer 203a to couple contact pads 250 to traces 205. In order to isolate the vias 255 from ground plane 202a, apertures 257 are formed in ground plane 202a through which vias 255 extend. In some embodiments, apertures 257 can be filled with an insulative material. In other various embodiments, apertures 257 can be hollow openings in the various layers through which vias 255 extend.

In various embodiments of the present disclosure, feedthrough assembly 200 can include a weld ring 235 to hermetically seal feedthrough assembly 200. Weld ring 235 can also be connected to the body of IMD such that there is a hermetic seal between IMD and feedthrough assembly 200. The weld ring 235 can be coupled to the feedthrough assembly in various manners, such as by braze joint, diffusion bond, glass seal or a compression seal. Furthermore, in various embodiments, feedthrough assembly 200 can include an integrated transceiver, similar to feedthrough assembly 20 described above and illustrated in FIG. 4.

The broad teachings of the disclosure can be implemented in a variety of forms. Therefore, while this disclosure includes particular examples, the true scope of the disclosure should not be so limited since other modifications will become apparent upon a study of the drawings, the specification, and the following claims.

What is claimed is:

1. A multilayered feedthrough for an implantable medical device, the feedthrough including a first edge and a second edge, comprising:

a substrate having a first edge corresponding to the first edge of the feedthrough, a second edge corresponding to the second edge of the feedthrough, a substrate length, a first surface and a second surface opposite the first surface, a first plurality of traces formed on the first surface and extending along the substrate length;

a second plurality of traces formed on the second surface and extending along the substrate length;

a first plurality of contact pads electrically coupled with the first plurality of traces;

a second plurality of contact pads electrically coupled with the second plurality of traces;

a first insulator layer formed on the first surface and the first plurality of traces;

a second insulator layer formed on the second surface and the second plurality of traces;

a first ground plane layer;

a second ground plane layer, wherein the first and second plurality of contact pads extend to the first and second edges of the feedthrough; and an integrated capacitor or filtering device, or both formed directly on the first surface of the substrate and the first insulator layer hermetically encasing the capacitor or the filtering device or both.

2. The multilayered feedthrough of claim 1, wherein the first plurality of traces includes at least one power line and at least one signal line for the integrated transceiver.

3. The multilayered feedthrough of claim 2, wherein the first plurality of contact pads and the second plurality of contact pads extend around the first and second edges of the substrate.

4. The multilayered feedthrough of claim 1, further comprising a third insulator layer formed on the first ground plane layer; and a fourth insulator layer formed on the second ground plane layer.

5. The multilayered feedthrough of claim 4, wherein the first and second plurality of contact pads are formed on the third and fourth insulator layers, respectively.

6. The multilayered feedthrough of claim 5, wherein a first plurality of vias electrically couple the first plurality of contact pads with the first plurality of traces, and a second plurality of vias electrically couple the second plurality of contact pads with the second plurality of traces.

7. The multilayered feedthrough of claim 1, wherein the first ground plane layer comprises a continuous layer of conductive material.

8. The multilayered feedthrough of claim 1, wherein the first ground plane layer comprises a mesh of conductive material.

9. The multilayered feedthrough of claim 1, wherein the substrate, the first insulator layer, and the second insulator layer comprise a non-conductive material.

10. The multilayered feedthrough of claim 9, wherein the non-conductive material comprises a high temperature co-fired ceramic.

11. The multilayered feedthrough of claim 1, wherein the substrate further includes a first edge portion proximate the first edge and a second edge portion proximate the second edge, the first and second insulator layers being absent from the first and second edge portions.

12. The multilayered feedthrough of claim 1, wherein the first and second plurality of contact pads are formed on the substrate.

13. An implantable medical device, comprising the multilayered feedthrough of claim 1.

14. The multilayered feedthrough of claim 1, wherein the first ground plane layer is electrically connected with one of the first plurality of traces.

15. A multilayered feedthrough for an implantable medical device, the feedthrough including a first edge and a second edge, comprising:

a substrate having a first edge corresponding to the first edge of the feedthrough, a second edge corresponding to the first edge of the feedthrough, and a substrate length, a plurality of traces formed on the substrate and extending along the substrate length;

a plurality of contact pads electrically coupled with the plurality of traces;

an insulator layer formed on the substrate and the plurality of traces;

a ground plane layer, wherein the plurality of contact pads extends to the first and second edges of the feedthrough; and an integrated capacitor or filtering device, or both formed directly on the substrate and the insulator layer hermetically encasing the capacitor or the filtering device or both.

16. The multilayered feedthrough of claim 15, wherein the plurality of traces includes at least one power line and at least one signal line for the integrated transceiver.

17. The multilayered feedthrough of claim 16, wherein the plurality of contact pads extend around the first and second edges of the substrate.

18. The multilayered feedthrough of claim 15, further comprising a second insulator layer formed on the ground plane layer.

19. The multilayered feedthrough of claim 18, wherein the plurality of contact pads are formed on the second insulator layer.

20. The multilayered feedthrough of claim 19, wherein a plurality of vias electrically couple the plurality of contact pads with the plurality of traces.

21. The multilayered feedthrough of claim 15, wherein the ground plane layer comprises a continuous layer of conductive material.

22. The multilayered feedthrough of claim 15, wherein the ground plane layer comprises a mesh of conductive material.

23. The multilayered feedthrough of claim 15, wherein the substrate, the insulator layer, and the second insulator layer comprise a non-conductive material.

24. The multilayered feedthrough of claim 23, wherein the non-conductive material comprises a high temperature co-fired ceramic.

25. The multilayered feedthrough of claim 15, wherein the substrate further includes a first edge portion proximate the first edge and a second edge portion proximate the second edge, the first and second insulator layers being absent from the first and second edge portions.

26. The multilayered feedthrough of claim 15, wherein the ground plane layer is substantially perpendicular to the first and second surfaces.

27. The multilayered feedthrough of claim 15, wherein the plurality of contact pads are formed on the substrate.

28. An implantable medical device, comprising the multilayered feedthrough of claim 15.

29. The multilayered feedthrough of claim 15, wherein the ground plane layer is electrically connected with one of the plurality of traces.

* * * * *